United States Patent [19]

Ponticello et al.

[11] 4,215,195
[45] Jul. 29, 1980

[54] POLYMERS OF AMIDE COMPOUNDS USEFUL IN PHOTOGRAPHIC MATERIALS

[75] Inventors: Ignazio S. Ponticello, Rochester; Kenneth R. Hollister, Pittsford; Richard C. Tuites, Rochester, all of N.Y.

[73] Assignee: Eastman Kodak Company, Rochester, N.Y.

[21] Appl. No.: 971,463

[22] Filed: Dec. 20, 1978

[51] Int. Cl.$^2$ ............................................. G03C 1/72
[52] U.S. Cl. .................................. 430/496; 430/510; 430/523; 430/905; 526/263
[58] Field of Search ................. 96/114, 115 P, 115 R; 204/159.14, 159.15; 260/239 BC; 526/263

[56] References Cited

U.S. PATENT DOCUMENTS

| | | | |
|---|---|---|---|
| 3,411,911 | 11/1968 | Dystra | 96/87 |
| 3,459,790 | 8/1969 | Smith | 260/483 |
| 3,488,708 | 1/1970 | Smith | 96/84 |
| 3,554,987 | 1/1971 | Smith | 260/79.3 |
| 3,658,878 | 4/1972 | Smith | 260/465.4 |
| 3,748,132 | 7/1973 | Arcesi | 96/115 P |
| 3,926,436 | 12/1975 | Monballo et al. | 96/67 |
| 4,106,941 | 8/1978 | Sculland et al. | 96/82 |

FOREIGN PATENT DOCUMENTS 1104658  2/1968  United Kingdom .
1130098  10/1968  United Kingdom .
1130581  10/1968  United Kingdom .

OTHER PUBLICATIONS

Research Disclosure, 13025, 2/75.

*Primary Examiner*—Jack P. Brammer
*Attorney, Agent, or Firm*—J. L. Tucker

[57] ABSTRACT

Compounds useful in making crosslinkable polymers having the formula (I):

$$CH_2=\overset{R}{\underset{|}{C}}-\overset{O}{\underset{\|}{C}}-Z-\overset{O}{\underset{\|}{C}}-CH_2-R^1$$

wherein R is hydrogen or methyl; $R^1$ is cyano or $$-\overset{O}{\underset{\|}{C}}R^2$$

wherein $R^2$ is alkyl; Z is $-X-R^3-X-$ or $$-N\overset{\cdot\cdot D_1\cdot\cdot}{\underset{\cdot\cdot D_2\cdot\cdot}{\bigcirc}}N-$$

wherein each $-X-$ is $-O-$ or $-NR^4-$, provided at least one $-X-$ is $-NR^4-$ wherein $R^4$ is hydrogen or alkyl, $R^3$ is divalent hydrocarbon and $D_1$ and $D_2$ together are the carbon atoms necessary to complete a 5 to 7 membered ring. These compounds can be homopolymerized or copolymerized with each other or with polymerizable ethylenically unsaturated monomers to give crosslinkable polymers. Such polymers can be purified by conventional purification techniques such as dialysis, diafiltration, ultrafiltration without losing their capability of crosslinking. The resulting purified polymers are particularly useful in photographic materials as gelatin extenders, binders or polymeric color couplers.

15 Claims, No Drawings

POLYMERS OF AMIDE COMPOUNDS USEFUL IN PHOTOGRAPHIC MATERIALS

BACKGROUND OF THE INVENTION

1. Field of the Invention

This invention relates to organic materials which are particularly useful in the photographic field. In one of its aspects, this invention relates to polymerizable compounds which can be used to form polymers. These polymers, in turn, can be incorporated into photographic materials to obtain a desirable combination of properties. In another of its aspects, this invention relates to photographic elements comprising these polymers.

2. Description of the Prior Art

Due to its good dispersing property and excellent protective colloid properties, gelatin has been used as a binding agent in layers of radiation sensitive elements for many years. Gelatin, however, is susceptible to dimensional change when subjected to varying environmental conditions, e.g., temperature and humidity. Many natural and synthetic polymeric materials such as vinyl polymers, have been proposed as substitutes for gelatin. However, use of these polymers in layers of elements, particularly photographic elements, often adversely affects layer hardness, resistance to abrasion and adhesion to film supports.

These problems are resolved in large measure with the polymers disclosed in U.S. Pat. Nos. 3,459,790 issued Aug. 5, 1969; 3,488,708 issued Jan. 6, 1970; 3,554,987 issued Jan. 12, 1971; and 3,658,878 issued Apr. 25, 1972, all to Smith. These patents relate to film-forming, addition polymers containing at least about 0.1 percent, by weight, of active methylene groups in aliphatic side chains. These polymers can be used as gelatin extenders or substitutes in photographic materials to yield products having dimensional stability and resistance to abrasion. These polymers are capable of crosslinking through the active methylene groups in the side chains. Particularly useful polymers disclosed in the Smith patents are those formed partially or wholly from 2-acetoacetoxyethyl methacrylate or 2-acetoacetoxyethyl acrylate.

The compounds disclosed in the Smith patents, particularly 2-acetoacetoxyethyl acrylate and 2-acetoacetoxyethyl methacrylate, copolymerize with other acrylic esters in a fairly random manner resulting in homogeneous copolymers. However, upon copolymerization with vinyl amides, they generally form nonhomogeneous copolymers. Such nonhomogeneous copolymers tend to have low molecular weight fragments of homopolymers of one of the comonomers. When these nonhomogeneous polymers are subjected to many conventional purification techniques, e.g., dialysis, diafiltration or ultrafiltration, to remove impurities, they lose most or all of their capability of crosslinking. The resulting polymers are then no longer useful as gelatin substitutes in photographic materials.

It is well known in the photographic arts that migration of integral hydrophilic color couplers from one layer to another can be minimized by attaching color couplers to polymers in some way. If these same polymers function as gelatin extenders or replacements, thin emulsion layers are possible. Thin emulsion layers are advantageous in saving storage and coating costs. Lipophilic color coupling copolymers are disclosed, for example, in British Patent Specification No. 1,130,098 published Oct. 9, 1968. U.S. Pat. No. 3,926,436 issued Dec. 16, 1975 to Monbaliu et al., discloses hydrophilic color coupling latex polymers made from various acrylamides substituted with sulfonic acids or salts. These polymers, however, lack crosslinking sites that are reactive with conventional gelatin hardeners.

Hence, it is desirable to have water-dispersible, crosslinkable polymers which can act simultaneously as polymeric color couplers, binders and gelatin extenders. It is also desirable that these polymers retain their capability of crosslinking after being subjected to such purification techniques as dialysis, dialfiltration and ultrafiltration.

SUMMARY OF THE INVENTION

This invention provides certain water-dispersible and crosslinkable polymers which retain their ability to crosslink and are dimensionally stable and resistant to abrasion after being subjected to conventional purification techniques. These polymers can act simultaneously as polymeric color couplers, binders and gelatin extenders. These polymers are formed from polymerizable compounds having amide groups and active methylene crosslinking sites in side chains extending from ethylenically unsaturated backbones. Many of the polymers, such as those wherein each —X— in the following formula (I) is —NR⁴—, have improved hydrolytic stability to high or low pH in comparison to prior art polymers that are now used as gelatin extenders in photography.

This invention provides a compound of formula (I):

wherein R is hydrogen or methyl; R¹ is cyano or

wherein R² is alkyl; Z is —X—R³—X— or

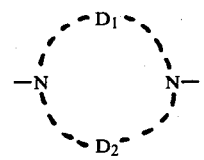

wherein each —X— is —O— or —NR⁴—, provided at least one —X— is —NR⁴—, wherein R⁴ is hydrogen or alkyl, R³ is divalent hydrocarbon and D₁ and D₂ together are the carbon atoms necessary to complete a 5 to 7 membered ring.

This invention also provides a crosslinkable polymer of at least one polymerizable compound of formula (I).

Further, this invention provides a radiation sensitive element comprising a support and having thereon at least one radiation sensitive layer and a crosslinkable polymer of at least one polymerizable compound of formula (I).

DESCRIPTION OF PREFERRED EMBODIMENTS

The polymerizable compounds of this invention are of the formula (I):

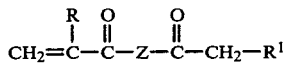

wherein R is hydrogen or methyl and preferably hydrogen; $R^1$ is cyano or

and preferably the latter, wherein $R^2$ is alkyl, preferably of 1 to 6 carbon atoms such as methyl, ethyl, isopropyl, t-butyl, 2-methylpentyl, hexyl; Z is —X—$R^3$—X— or

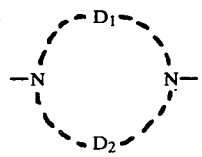

wherein each —X— is —O— or —$NR^4$—, provided at least one —X— is —$NR^4$—, and $R^4$ is hydrogen or alkyl, preferably of 1 to 6 carbon atoms as defined for $R^2$. Preferably, Z is —NH—$R^3$—O—.

$R^3$ is divalent hydrocarbon such as alkylene, preferably of 1 to 12 carbon atoms, branched or linear, such as methylene, ethylene, propylene, 2,2-dimethyl-1,3-propylene, 2,2-dimethyl-1,6-hexylene, decylene, etc.; arylene, preferably of 6 to 12 carbon atoms, such as phenylene, naphthylene, xylylene, etc.; arylenebisalkylene, preferably of 8 to 32 carbon atoms, such as phenylenedimethylene, phenylenedibutylene, naphthylenedihexylene, phenylenedi-tert-butylene, etc.; alkylenebisarylene, preferably of 13 to 34 carbon atoms, such as methylenediphenylene, butylenedinaphthylene, isopropylidenediphenylene, etc.; arylenealkylene, preferably of 7 to 24 carbon atoms, such as phenylenemethylene, phenylenepropylene, phenyleneisobutylene, naphthylenemethylene, etc.; cycloalkylene, preferably of 4 to 12 carbon atoms, such as cyclobutylene, cyclopentylene, cyclohexylene, etc. and other similar divalent hydrocarbons within the skill of an ordinary worker in the art. Any of these divalent hydrocarbons can have one or more branched portions or cycloalkylenes, preferably of 5 to 10 carbon atoms, interposed in the main chain, and can be substituted with one or more of a variety of inert substituents known to those skilled in the art which will not adversely affect the desired properties of the compounds. Preferably, $R^3$ is alkylene, arylene, arylenealkylene, arylenebisalkylene or alkylenebisarylene. More preferably, $R^3$ is alkylene.

In the definition of Z, $D_1$ and $D_2$ together are the carbon atoms necessary to complete a 5 to 7 membered ring. These heterocyclic rings can be substituted with one or more alkyl groups, each preferably of from 1 to 4 carbon atoms. Z can typically be,

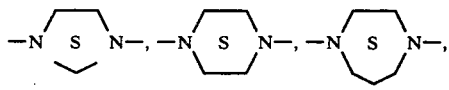

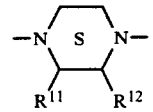

wherein each of $R^{11}$ and $R^{12}$ is alkyl, preferably of 1 to 4 carbon atoms, etc., and preferably is

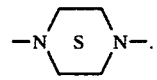

Exemplary monomeric compounds within the scope of formula (I) are N-(2-cyanoacetoxyethyl)acrylamide, 4-cyanoacetyl-1-methacryloylpiperazine, N-(2-propionylacetoxybutyl)acrylamide, N-(2-valerylacetoxyphenyl)acrylamide, N-4-(acetoacetoxymethyl)benzyl acrylamide, N-4-(acetoacetoxybenzyl)phenyl methacrylamide, N-(2-acetoacetoxyethyl)acrylamide, N-(3-acetoacetamidopropyl)methacrylamide, N-(2-acetoacetamidoethyl)methacrylamide, 4-acetoacetyl-1-methacryloylpiperazine, acetoacetamidoethyl methacrylate, 4-acetoacetyl-1-acryloylpiperazine, N-(2-propionylacetoxyethyl)acrylamide, N-(2-valerylacetoxypropyl)methacrylamide, etc.

In general, compounds within the scope of formula (I) can be prepared by treating an amine salt containing a reactive methylene group with a methacryloyl or acryloyl halide (chloride, bromide, etc.), or by reacting an appropriate amine salt of an acrylamide or methacrylamide, acrylate or methacrylate with diketene. Particular conditions for preparing compounds by these techniques are illustrated in the following Examples 2-6.

Certain compounds of this invention, namely those of formula (II):

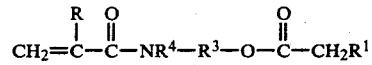

wherein R, $R^1$ and $R^4$ are as defined hereinbefore for formula (I) and $R^3$ is alkylene can be made by the following method. This method comprises the steps of:

(a) reacting cyclopentadiene with either (i) an alkenoic acid halide such as

etc. in a suitable organic solvent, e.g. dichloromethane, trichloromethane, acetone, diethyl ether, tetrahydrofuran, benzene, toluene, etc. at 20° C. and 760 mm Hg for from about 15 minutes to about 24 hours in a molar ratio ranging from about 2:1 to about 1:2, or (ii) an alkyl acrylate, e.g. methyl acrylate, ethyl acrylate, methyl methacrylate, ethyl methacrylate, etc., under similar conditions to form either endo- and exo-norborene-5-carboxylic acid halides or alkyl endo- and exo-norborene-5-carboxylates;

(b) either (i) reacting the product obtained from step (a) (i) with an alkanolamine, of the formula

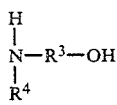

wherein R³ and R⁴ are as defined hereinbefore for formula (II), e.g. ethanolamine, propanolamine, isobutanolamine, methylethanolamine, etc., in the presence of an acid acceptor, e.g. triethylamine, tributylamine, tripropylamine, pyridine, etc., in a suitable organic solvent e.g. chloroform, dichloromethane, diethyl ether, tetrahydrofuran, toluene, acetone, etc., at 20° C. and 760 mm Hg for from about 10 minutes to about 24 hours at a molar ratio of from about 1:1 to about 1:2; or (ii) reacting the product obtained from step (a) (ii) with an alkanolamine with or without a suitable catalyst, e.g. ammonium chloride, triethylamine hydrochloride, etc., using the same times and ratios as in (b) (i), but at a temperature in the range from about 20° C. to the reflux temperature of the solvent;

(c) reacting the product obtained from step (b) with a diketene, such as

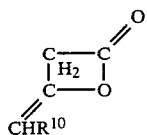

wherein $R^{10}$ is hydrogen or alkyl, preferably of 1 to 5 carbon atoms, such as methyl, ethyl, isopropyl, t-butyl, chloromethyl, etc., or with cyanoacetyl chloride in the presence of a trialkylamine, e.g. tributylamine, etc., in a suitable organic solvent, e.g. tetrahydrofuran, acetone, diethyl ether, N,N-dimethylformamide, benzene etc., at 20° C. and 760 mm Hg for from about 1 to about 24 hours at a molar ratio of product of step (b) to diketene or chloride of from about 1:1 to about 1:2; and (d) subjecting the product obtained from step (c) to thermal cracking by passing it through a cracking quartz column at a flow rate of about 0.5 drop/sec. to about 1.0 drop/min., at a temperature in the range of from about 400° to about 800° C. at a reduced pressure in the range of from about 1μ to about 2 mmHg.

The method just described is particularly useful because it allows one to prepare the compounds of formula (II) while avoiding premature polymerization.

The particular conditions of this method are illustrated in the following Example 1.

The described polymerizable compounds are useful in preparing the crosslinkable polymers of this invention. In general, these polymers are film formers and water-dispersible. These polymers are prepared from at least about 0.1 percent, by weight, of one or more of these compounds. Preferred polymers include those prepared from compounds having the previously indicated preferred R, R¹ and Z radicals of formula (I).

In addition, the polymers of this invention can be formed of at least one polymerizable compound of formula (I) polymerized with up to about 99.9 percent, by weight, of at least one additional ethylenically unsaturated polymerizable monomer. Typically, these monomers are those containing at least one —CH=C> or CH₂=C> radical. Exemplary additional monomers include, for example, vinyl esters, e.g. vinyl acetate, vinyl butyrate, etc.; vinyl amides, e.g. acrylamide, methacrylamide, N-methylacrylamide, N-isopropylmethacrylamide, etc.; vinyl nitriles, e.g. acrylonitrile, methacrylonitrile, 3-butenenitrile, etc.; vinyl ketones, e.g. methyl vinyl ketone, diacetone acrylamide, etc.; vinyl halides, e.g. vinyl chloride, vinyl bromide, vinylidene chloride, etc.; vinyl ethers, e.g. allyl methyl ether, allyl phenyl ether, 2-chloro-vinyl methyl ether, etc.; alpha-beta-unsaturated acids or esters thereof, e.g. acrylic acid, methacrylic acid, methyl acrylate, butyl methacrylate, 2-dimethylaminoethyl methacrylate, 2-ethylhexyl acrylate, 2-hydroxyethyl methacrylate, etc.; olefins and diolefins, e.g. ethylene, propylene, butadiene, isoprene, 1,1-diphenylethylene, etc.; vinyl aromatics, e.g. styrene, α-methylstyrene, p-chlorostyrene, etc.; 4,4,9-trimethyl-8-oxo-7-oxa-4-axonia-9-decene-1-sulfonate; N-vinylsuccinamide; N-vinylphthalimide; N-vinylpyrazolidone; and others known in the art.

Preferably, the polymers of this invention are prepared from about 2 to about 30 percent, by weight, of at least one compound of formula (I) polymerized with about 70 to about 98 percent, by weight, of at least one additional ethylenically unsaturated polymerizable monomer.

In a preferred embodiment of this invention, the additional ethylenically unsaturated polymerizable monomers are selected from the following groups of monomers:

(a) acrylamides of the formula (III):

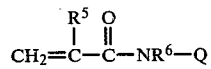

wherein each of R⁵ and R⁶ is hydrogen or alkyl, preferably of 1 to 6 carbon atoms, e.g. methyl, ethyl, isopropyl, etc., and Q is a radical capable of undergoing oxidative coupling with a primary amino compound;

(b) sulfoesters or sulfonamides having the formula (IV):

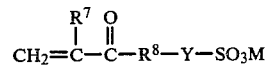

wherein R⁷ is hydrogen or alkyl, preferably of 1 to 6 carbon atoms, R⁸ is —O— or —NR⁹— wherein R⁹ is hydrogen or alkyl, preferably of 1 to 6 carbon atoms, Y is a divalent aliphatic, alicyclic or aromatic radical, preferably a divalent hydrocarbon of 1 to 10 carbon atoms, but optionally containing oxygen or sulfur atoms; and M represents a monovalent cation such as hydrogen, an alkali metal atom, e.g. sodium and potassium, ammonium or an organic onium cation, e.g. tetramethylammonium, etc.; and (c) amides of ethylenically unsaturated carboxylic acids, each amide having a formula different from formula (III) or (IV).

Oxidative coupling is the formation of a colored dye by reaction of the semiquinone moiety of a phenylenediamine with a nucleophile. It is understood in the art that, in the photographic process, a nucleophile precursor, such as a color coupler, becomes a nucleophile under development conditions, that is, in the presence of an alkali.

Representative divalent radicals for Y include alkylene, cycloalkylene, arylene, alkylene-oxy-alkylene, alkylenearylene, alkylenethioalkylene and alkyleneoxyarylene, etc. The alkylene radicals are preferably straight- and branched-chain alkylene groups of 1 to 6 carbon atoms, and can be substituted with halogens, alkoxy or phenyl.

Representative monomers of group (a) include those prepared from reaction of color coupling compounds having a reactive substituent in a position other than the coupling position with an acrylic monomer having an acid or acid halide reactive site. Typical reactive substituents on the coupling compounds are amino or sulfonamido. Typical acrylic monomers are acryloyl chloride, methacryloyl chloride, acrylic acid, etc. Other monomers of group (a) can be prepared by grafting color coupling compounds onto active methylene group-containing monomers having suitable reactive sites such as an acid or acid halide. Typical color coupling compounds useful in preparing group (a) monomers are well known in the art, including the color coupling compounds disclosed, for example, in U.S. Pat. Nos. 2,295,009; 2,367,531; 2,423,730; 2,474,293; 2,772,162; 2,895,826; 2,920,961; 3,002,836; 3,013,879; 3,244,520; 2,600,788; 3,152,896; 3,127,269; 3,519,429; 2,908,573; 3,875,057; 2,407,210; 3,265,506; and 3,926,436; and British Pat. Nos. 1,248,924; and 1,111,554.

Particularly useful group (a) monomers are those wherein Q is one of the following color coupling radicals:

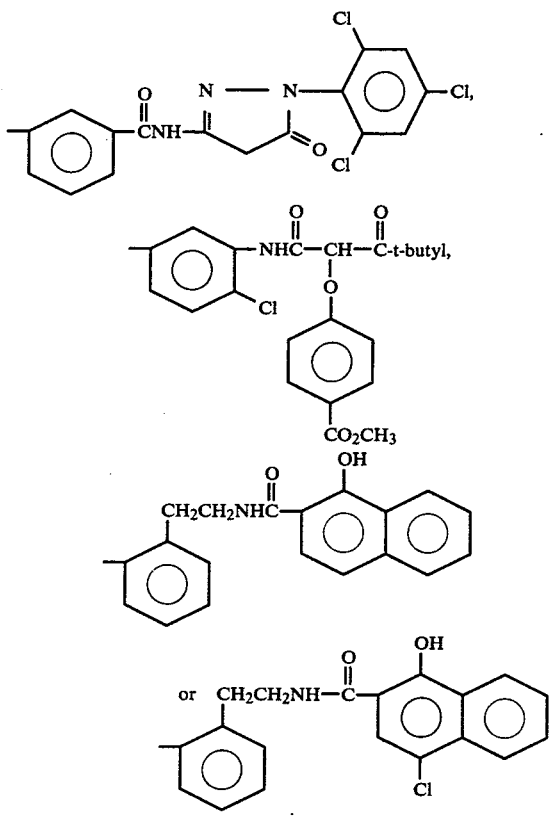

Preferred monomers of group (a) include 2'-[2-(1-hydroxy-2-naphthoylamino)ethyl]acrylanilide, 4'-chloro-3'-[α-(4-methoxycarbonylphenoxy)-α-pivaloylacetamido]acrylanilide and 1-(2,4,6-trichlorophenyl)-3-(3-acrylamidobenzamido)-2-pyrazoline-5-one.

Representative monomers of group (b) include 2-acrylamido-2-methylpropane-1-sulfonic acid and its sodium salt, 3-acryloyloxypropane-1-sulfonic acid and its sodium salt, 3-methacryloyloxypropane-1-sulfonic acid and its potassium salt, 4-acryloyloxybutane-2-sulfonic acid and its sodium salt, and others disclosed in U.S. Pat. Nos. 3,024,221 and 3,411,911 and British Specification No. 1,009,186. Preferred monomers include 2-acrylamido-2-methylpropane-1-sulfonic acid and its sodium salt.

Representative monomers of group (c) include acrylamide, methacrylamide, diacetone acrylamide, N-methylacrylamide, N-isopropylacrylamide, and others known in the art. A preferred monomer is acrylamide.

Representative polymers of this invention include poly[N-(2-acetoacetoxyethyl)acrylamide], poly[N-(2-cyanoactoxypropyl)methacrylamide], poly(N-(3-acetoacetamidopropyl)methacrylamide], poly[4-acetoacetyl-1-methacryloylpiperazine], poly[acrylamide-co-N-(2-acetoacetoxyethyl)acrylamide], poly[N-isopropylacrylamide-co-2-acrylamido-2-methylpropane-1-sulfonic acid, sodium salt-co-N-(2-acetoacetoxyethyl)acrylamide], poly[2-acrylamido-2-methylpropane-1-sulfonic acid, sodium salt-co-2'-[2-(1-hydroxy-2-naphthoylamino)ethyl]-acrylanilide-co-N-(2-acetoacetoxyethyl)acrylamide], poly[2-acrylamido-2-methylpropane-1-sulfonic acid, sodium salt-co-4'-chloro-3'-[α-(4-methoxycarbonylphenoxy)-α-pivaloylacetamido]acrylaniline-co-N-(2-acetoacetoxyethyl)acrylamide], poly[2-acrylamido-2-methylpropane-1-sulfonic acid, sodium salt-co-1-(2,4,6-trichlorophenyl)-3-(3-acrylamidobenzamido)-2-pyrazoline-5-one-co-N-(2-acetoacetoxyethyl)acrylamide], poly[acrylamide-co-acetoacetamidoethyl methacrylate], poly[methacrylic acid-co-N-(2-acetoacetoxyethyl)acrylamide], etc.

The polymers of this invention are characterized by having inherent viscosities typically in the range of from about 0.1 to about 3.0, and preferably from about 0.2 to about 2.0, as measured by standard techniques in N,N-dimethylformamide, acetone, or 1 N sodium chloride at a concentration of 0.25 g/dl of solution at 25° C.

The polymerization conditions which can be used for making the polymers of this invention are those commonly employed in polymerization techniques known in the art, including emulsion, suspension and solution techniques. Polymerization temperature is subject to wide variation as it depends upon several variables, but it is generally in the range of from about 20° C. to 120° C. The pressure employed in the polymerization, if any, is usually only sufficient to maintain the reaction mixture in liquid form. The polymerization can be carried out in a suitable vehicle, for example, in water or mixtures of water with water miscible solvents, e.g. methanol, ethanol, propanol, isopropanol, butanol, etc., or in an organic solvent or in mixtures of organic solvents, e.g. N,N-dimethylformamide, acetone, dimethyl sulfoxide, etc. Generally, the concentration of polymerizable compound or monomer in the polymerization solution or emulsion is up to about 40%, by weight, and preferably from about 10 to about 25%, by weight, based on the total weight. Suitable catalysts include free radical catalysts, e.g. hydrogen peroxide, cumene hydroperoxide, water soluble azo type initiators, etc. In redox polymerization systems, the usual ingredients can be employed. If desired, the polymer can be isolated from reaction medium by freezing, salting out, precipitation or any other procedure suitable for this purpose.

It is sometimes advantageous to use a surface active agent or compatible mixtures of such agents in the preparation of vinyl or addition polymers and in coating photographic materials containing such polymers. Suitable agents include the non-ionic, ionic and amphoteric types known in the art.

Specific conditions for making the polymers of this invention are illustrated in the following Examples 7-15, 17 and 18.

The polymers of the present invention are useful in a variety of materials including both radiation sensitive and non-radiation sensitive materials. Examples of non-radiation sensitive materials include diffusion transfer receiver sheets, clinical assay elements, adhesive layers and the like. The polymers can be used therein as binders or binder extenders. Similarly, they can be used as binders, gelatin and other binder extenders, polymeric color couplers or other polymeric adjuvants in a variety of radiation sensitive materials, e.g. lithographic plates, photoresists and electrophotographic, electrographic, x-ray and photographic elements.

In a preferred embodiment of this invention, these polymers are useful as binders, extenders for hydrophilic colloids or polymeric color couplers in one or more layers of photographic materials. Examples of such photographic materials and their composition are known in the art, and disclosed, for example, in *Product Licensing Index*, Vol. 92, December, 1971, publication 9232, pp. 107-110, and *Research Disclosure*, No. 151, November, 1976, publication 15, 162, pp. 75-87, both published by Industrial Opportunities, Ltd., Homewell, Havant Hampshire PO9 LEF, United Kingdom.

When used in photographic layers, the polymers of this invention are generally mixed with other binding agents, such as natural or synthetic resins, gelatin or other hydrophilic colloids. Generally, the concentration of the polymers is in the range of from about 20 to about 85%, and often in the range of from about 50 to about 85%, by weight, based on total binding agent (dry weight). Preferably, the polymers are mixed with gelatin.

The polymers of this invention can be used simultaneously as polymeric binders and color couplers in color image-forming emulsions when the polymers are prepared with group (a) monomers described hereinbefore. The Q moieties incorporated into those polymers are capable of reacting with suitable developing agents, e.g. p-phenylenediamine and derivatives, including N,N-diethyl-p-phenylenediamine, N-butyl-N-sulfobutyl-p-phenylenediamine, 2-amino-5-diethylaminotoluene, 4-amino-N-ethyl-N-($\beta$-methanesulfonamidoethyl)-m-toluidine, N-hydroxyethyl-N-ethyl-p-phenylenediamine and the like.

This invention is further illustrated by the following examples of its practice.

EXAMPLE 1

Preparation of N-(2-acetoacetoxyethyl)-acrylamide

Step 1

A cooled solution ($-78°$ C.) of acryloyl chloride (362 g, 4.0 moles) and freshly distilled cyclopentadiene (280 g, 4.3 moles) in dichloromethane (750 ml) was warmed in a reaction vessel to 20° C. The resulting exothermic reaction was allowed to proceed for about 12 hours, and subsequently the reaction mass was heated to distill off the solvent. Upon distillation of the residue from the mass, endo- and exo-5-norbornene-2-carbonyl chlorides (b.p. 45° to 50° C./1.5 mm) were recovered. The yield was 95%.

Step 2

The products of Step 1 (500 g, 3.2 moles) were added gradually to a solution of ethanolamine (200 g, 3.6 moles) and triethylamine (360 g, 3.6 moles) in chloroform (2 l.) in a cooled reaction vessel. The reaction mass was stirred for 24 hours at 20° to 25° C. The resulting solution was treated with two 250 ml portions of NaHCO$_3$, dried over MgSO$_4$, filtered and distilled to remove the chloroform. Endo- and exo-5-[N-(2-hydroxyethyl)-carbamoyl]-2-norbornenes (b.p. 121° to 135° C./10 mm) were recovered in 85% yield.

Step 3

A solution of the Step 2 products (90.5 g, 0.5 moles), diketene (57.0 g, 0.7 moles), and tributylamine (2 g) in tetrahydrofuran (500 ml) was refluxed for 3 hours in a reaction vessel and then kept at 20° to 25° C. for 12 hours to form the Diels-Alder adducts, endo- and exo-5-[N-(2-acetoacetoxyethyl)carbamoyl]-2-norbornenes.
The tetrahydrofuran was distilled from the reaction mass and 500 ml of chloroform was added. The resulting solution was treated first with 5 percent HCl (250 ml), and then with two portions of NaHCO$_3$ (250 ml), dried with anhydrous MgSO$_4$ and filtered. The chloroform was removed by distillation.

Step 4

The residue from Step 3 was then subjected to thermal cracking by passing it in a 3- to 4-hour period downwardly through a vertical quartz tube (30.5 cm. by 2.54 cm.) packed with quartz chips maintained at 650° C. The products from the tube were collected under reduced pressure (2 mm Hg) in a receiving vessel maintained at $-20°$ C. Distillation of the recovered material yielded N-(2-acetoacetoxyethyl)acrylamide (b.p. 108° to 132° C./2 mm).

The same product was obtained when cyclopentadiene was reacted with methyl acrylate instead of the chloride in Step 1.

EXAMPLE 2

Preparation of N-(2-acetoacetamidoethyl)-methacrylamide

Step 1

A mixture of ethylenediamine (60 g, 1 mole), water (250 ml), methanol (500 ml) and Bromophenol Blue solution was acidified to pH 3 (yellow color) with hydrochloric acid (165 ml, 12 N). While the resulting solution was vigorously stirred at 25° C., benzyl chloroformate (100.6 g, 0.59 mole) was added dropwise (addition time 1.75 hours). Sodium hydroxide (210 ml, 5 N) was added as required to maintain the solution at pH 3.0-4.5. The methanol was removed at reduced pressure and the reaction mixture was filtered. The aqueous filtrate was extracted once with benzene, and the benzene extract was discarded. The aqueous solution was cooled in a salt-ice bath, layered with ether and treated with sodium hydroxide (130 ml, 10 N) to pH 11-13. Three layers formed: an ether layer, an aqueous layer, and an oily blue layer. The aqueous layer was separated and extracted four times with portions of ether. The ether layer and ether extracts were combined with the oily blue layer and the ether removed using water pump vacuum. An oil pump was then used at 25° C. until the pressure dropped to 0.6 ppm. During this time, water and ethylenediamine were removed by distillation. The residue left in the flask consisted of an oil and a small amount of solid. After the mixture was filtered, 60 g (54% yield) of benzyl N-(2-aminoethyl)carbamate were obtained. This crude oil worked satisfactorily in the next step without further purification. See C. M. Hoffmann and S. R. Sapir, *Journal of Organic Chemistry*, 27, 3565 (1962) for further discussion of this preparatory method.

Step 2

A solution of benzyl N-(2-aminoethyl)carbamate (54 g, 0.276 mole) in ether (250 ml) and a solution of diketene (25.2 g, 0.30 mole) in ether (250 ml) were added simultaneously, dropwise, to ether (600 ml) while stirring and cooling over a 30 minute period. A white precipitate appeared. The solution was stirred 30 minutes longer, and then filtered. One recrystallization from water gave pure benzyl N-(2-acetoacetamidoethyl)carbamate (m.p.=116°-118° C.) at a yield of 90%.

Step 3

A mixture of benzyl N-(2-acetoacetamidoethyl)-carbamate (70.0 g, 0.25 mole) and hydrogen bromide-acetic acid solution (500 ml, 30-35%) was allowed to stand at 20° C., with occasional shaking for 1 hour, to allow complete evolution of carbon dioxide. A large volume of ether was added, and the oil which separated was triturated with fresh portions of ether. This crude product was then used in the next step without further purification.

Step 4

Crude N-(2-aminoethyl)acetoacetamide hydrobromide (50 g, 0.18 mole) was dissolved in N,N-dimethylformamide (500 ml). Triethylamine (78 g, 0.4 mole) and methacryloyl chloride (19 g, 0.18 mole) were added simultaneously at 0° C. The reaction solution was then stirred at 0° C. for 1 hour and at 20° C. for 20 hours. The resulting solution was filtered, the solvent removed, and the residue dissolved in chloroform (500 ml). The solution was then washed with 10% hydrochloric acid (200 ml), then water (200 ml) and dried over anhydrous magnesium sulfate. The solvent was then removed. The residue was recrystallized from ethanol/ether (1:1). The resulting compound had a m.p. of 86°-90° C. The yield was 25%.

EXAMPLE 3

Preparation of 4-Acetoacetyl-1-methacryloylpiperazine

Crude 1-acetoacetylpiperazine hydrobromide (50 g, 0.2 mole) was dissolved in N,N-dimethylformamide (300 ml) with Aranox ™ (50 mg) (available from U.S. Rubber Co.). Triethylamine (50 g, 0.5 mole) was added at 0° C., followed immediately by the dropwise addition of methacryloyl chloride (20.8 g, 0.2 mole) at 0° C. The reaction solution was then allowed to reach 20° C. over a 20 hour period. The reaction solution was filtered and the solvent was removed at low vacuum. The residue was distilled to give 4-acetoacetyl-1-methacryloylpiperazine (b.p.=110°-129° C./10-8µ) at a yield of 56%.

EXAMPLE 4

Preparation of 4-Acetoacetyl-1-acryloylpiperazine

This material was prepared by the technique described above in Example 3, except that acryloyl chloride was used instead of methacryloyl chloride. Although the resulting piperazine polymerized during distillation, it can be isolated by other standard techniques.

EXAMPLE 5

Preparation of acetoacetamidoethyl methacrylate

Pyridine (16 g, 0.2 mole) was added dropwise at 0° C. to a solution of 2-aminoethyl methacrylate hydrochloride (33 g, 0.2 mole) and diketene (16.8 g, 0.2 mole) in N,N-dimethylformamide (600 ml). After the addition, the solution was stirred at 20° C. for 20 hours. The solvent was then removed at low vacuum. The residue was dissolved in chloroform (1200 ml), washed with water (twice with 200 ml), dried over anhydrous magnesium sulfate and filtered. Excess solvent was then removed. Distillation of the residue gave acetoacetamidoethyl methacrylate (b.p.=113°-132° C./5µ) at a yield of 60%.

EXAMPLE 6

Preparation of N-(3-acetoacetamidopropyl)-methacrylamide

Triethylamine (24 g, 0.24 mole) was added dropwise at 0° C. to a solution of N-(3-aminopropyl)-methacrylamide hydrochloride (40 g, 0.24 mole) and diketene (20 g, 0.24 mole) in methanol (800 ml). After addition, the temperature was maintained at 0° C. for 2 hours under stirring. Stirring was continued at 20° C. for 20 hours. The solvent was then removed. The residue was dissolved in chloroform (1 liter), washed with 5% hydrochloric acid (200 ml), washed with saturated $NaHCO_3$ (200 ml), dried over anhydrous magnesium sulfate, and filtered. Excess solvent was removed. The residue was recrystallized from benzene (500 ml) and ethyl ether (500 ml) to give N-(3-acetoacetamidopropyl)methacrylamide (m.p.=93°-94° C.) at a yield of 50%.

EXAMPLE 7

Preparation and Use of Poly{N-(2-acetoacetoxyethyl)acrylamide}

A solution of N-(2-acetoacetoxyethyl)acrylamide (10.0 g, 0.05 mole) acetone (100 ml) and 2,2'-azobis(2-methylpropionitrile) (250 mg) was heated at 60°-65° C. for 3 hours. The resulting polymer (I.V.=1.34 in acetone) was precipitated from solution with isopropyl alcohol (4:1), filtered, washed, dried and quickly redissolved in acetone (8.2% solids). The yield was 80%.

Treatment of this polymer (2 ml) with 2 drops of formaldehyde solution (30-35%) and a drop of dilute base produced a crosslinked polymer. A coating of this polymer on gelatin-subbed poly(ethylene terephthalate) film produced clear, crosslinked film that would not wash off with water.

EXAMPLE 8

Preparation of Poly{N-(3-acetoacetamidopropyl)methacrylamide}

A solution of N-(3-acetoacetamidopropyl)methacrylamide (5.0 g, 0.22 mole), water (30 ml), and 4,4'-azobis(4-cyanovaleric acid) (125 mg. 65%) was heated at 60°-65° C. for 4 hours. The resulting polymer was purified by dialysis for 6 hours (9.2 solids). The yield was 80%.

EXAMPLE 9

Preparation of Poly[acetoacetamidoethyl methacrylate]

A solution of methacryloyloxyethylacetoacetamide (2.5 g, 0.012 mole), water (30 ml), and 4,4'-azobis(4-cyanovaleric acid) (50 mg, 65%) was heated at 60°–65° C. for 4 hours. The resulting polymer was purified by dialysis for 6 hours (2.4% solids). The yield was 70%.

EXAMPLE 10

Preparation of Poly[acrylamide-co-N-(2-acetoacetoxyethyl)acrylamide]

Acrylamide (45.0 g, 0.63 moles), N-(2-acetoacetoxyethyl)acrylamide (5.0 g, 0.025 moles) and 2,2'-azobis(2-methyl-propionitrile) (0.5 g) were mixed in water (400 ml) and absolute alcohol (40 ml) in a reaction vessel. The reaction mass was maintained at 60° to 65° C. for about 30 minutes until the reaction mass became highly viscous. Additional water (200 ml) was then added to reduce the viscosity. The reaction mass was then maintained at 60° to 65° C. for an additional 2.5 hours. Poly[acrylamide-co-N-(2-acetoacetoxyethyl)acrylamide] was formed in solution. Isopropyl alcohol (4 gal.) was added to the solution to precipitate the polymer (I.V.=1.07 in 1 N NaCl) which was subsequently filtered from the aqueous base, washed with water, and dried. The yield was 80%.

EXAMPLE 11

Preparation and Use of Poly[acrylamide-co-N-(3-acetoacetamidopropyl)methacrylamide]

A solution of N-(3-acetoacetamidopropyl)methacrylamide (2.0 g, 0.009 mole), acrylamide (18.0 g, 0.25 mole), water (150 ml), absolute ethanol (20 ml) and 4,4'-azobis(4-cyanovaleric acid) (450 mg, 65%) was maintained at 60°–65° C. for 1½ hours. The resulting polymer (I.V.=1.64 in 1 N NaCl) was precipitated from solution with acetone (4 l), filtered, washed, dried, and quickly redissolved in water (9.2% solids). The yield was 90%.

Treatment of this polymer (2 ml) with 2 drops of formaldehyde solution (30–35%) and a drop of dilute base crosslinked the polymer within seconds. With the addition of excess base (pH 13), the polymer remained crosslinked even after keeping it in a 65° C. water bath for 20 hours.

EXAMPLE 12

Preparation and Use of Poly[acrylamide-co-4-acetoacetyl-1-methacryloylpiperazine]

A solution of 4-acetoacetyl-1-methacryloylpiperazine (2.0 g, 0.0065 mole), acrylamide (18.0 g, 0.25 mole), water (180 ml), absolute ethanol (20 ml), and 4,4'-azobis(4-cyanovaleric acid) (500 mg, 65%) was maintained at 60°–65° C. for 20 hours. The resulting polymer was precipitated from solution with acetone (3.5 l) filtered, washed, dried and quickly redissolved in water (9.7% solids). The yield was 95%.

Treatment of this polymer (2 ml) with 4 drops of dilute base and 3 drops of formaldehyde solution (30–35%) crosslinked the polymer within seconds. With the addition of excess base (pH 13), the polymer solubilized in water in about 1½ hours.

EXAMPLE 13

Preparation of Poly[N-isopropylacrylamide-co-2-acrylamido-2-methylpropane-1-sulfonic acid, sodium salt-co-N-(2-acetoacetoxyethyl)acrylamide]

A solution of N-isopropylacrylamide (15.8 g, 0.14 mole), 2-acrylamido-2-methylpropane-1-sulfonic acid, sodium salt (9.2 g, 0.04 mole), N-(2-acetoacetoxyethyl)acrylamide (4.0 g, 0.002 mole) water (300 ml), absolute ethanol (30 ml) and 2,2'-azobis(2-methylpropionitrile) (300 mg) was maintained at 60° to 65° C. for about 12 hours. The resulting solution of polymer was dialyzed for 6 hours and concentrated to 7.4% solids.

EXAMPLE 14

Preparation of Poly[acrylamide-co-2-acrylamido-2-methylpropane-1-sulfonic acid, sodium salt-co-N-(2-acetoacetoxyethyl)acrylamide]

A solution of acrylamide (10.0 g, 0.14 mole), 2-acrylamido-2-methylpropane-1-sulfonic acid, sodium salt (9.2 g, 0.04 mole), N-(2-acetoacetoxyethyl)acrylamide (4.0 g, 0.02 mole), water (200 mol), absolute ethanol (20 ml) and 2,2'-azobis(2-methylpropionitrile) (200 mg) was maintained at 60°–65° C. for 20 hours. The resulting product was dialyzed for 6 hours and concentrated to 7.6% solids. The yield of polymer was 90%.

EXAMPLE 15

Preparation of a Cyan Dye Forming Polymeric Coupler Poly{2-acrylamido-2-methylpropane-1-sulfonic Acid, sodium salt-co-2'-[2-(1-hydroxy-2-naphthoylamino)ethyl]acrylanilide-co-N-(2-acetoacetoxyethyl)acrylamide} (Weight ratio 60:35:5)

A solution of 6.00 g of 2-acrylammido-2-methylpropane-1-sulfonic acid, sodium salt, 3.50 g of coupler monomer 2'-[2-(1-hydroxy-2-naphthoylamino)-ethyl]acrylanilide, 0.50 g of N-(2-acetoacetoxyethyl)acrylamide, and 0.05 g of 2,2'-azobis(2-methylpropionitrile) in 40 ml of N,N-dimethylformamide was sparged with high purity nitrogen for 15 minutes and kept in a 60° C. bath under nitrogen for 4 hours. The clear viscous polymer-containing dope which resulted was divided into two portions. Portion I was run in a fine stream into a large excess of diethyl ether with stirring. Particles of the polymer precipitated in the ether in the form of tan solids which were filtered from the ether, washed with fresh ether, and dried at room temperature. The polymer was recovered as a crisp light tan powder which was readily soluble in water and had an I.V. of 0.78 in N,N-dimethylformamide.

Portion II of the dope was placed in a cellulosic dialysis bag and dialyzed against flowing distilled water for 20 hours. A clear aqueous solution of dialyzed polymer was obtained. The isolated polymer was a light powder similar to that recovered from portion I of the dope.

EXAMPLE 16

Use of Cyan Polymer Coupler

One gram of each portion of isolated polymer obtained in Example 15 was dissolved in separate portions of distilled water (9 ml) and the pH of each resulting dope adjusted to 6.0. Each dope was treated with 25 drops of a 1% aqueous formaldehyde solutioN (providing 0.01 g of formaldehyde) and 11 drops of a 2.5% aqueous solution of a surfactant, para-isononylphenoxypolyglycidol (Surfactant 10G, available from Olin Chemical Co.) Each of the dopes was then coated on separate samples of gelatin-subbed poly(ethylene terephthalate) film base to a thickness of 6 mils and allowed to set. Upon reaching the dry state, each coating was found to have hardened into a clear, colorless, flexible, non-tacky layer of crosslinked polymer.

Each coated film base prepared as described was soaked in distilled water and washed in flowing distilled water to determine the durability of the coatings of the hardened polymers. The coatings remained intact even when rubbed vigorously and could be removed only by scraping them with a metal spatula. Samples of each scraping of hardened polymer were found to be insoluble in water.

Bis(vinylsulfonylmethyl) ether was used as a hardening agent for the polymers in a repeat of this Example. Substantially identical results were obtained.

EXAMPLE 17

Preparation and Use of a Yellow Dye Forming Polymeric Coupler,
POly{2-acrylamido-2-methylpropane-1-sulfonic acid, sodium salt-co-4'-chloro-3'-[α-(4-methoxycarbonylphenoxy)-α-pivaloylacetamido]acrylanilide-co-N-(2-acetoacetoxyethyl)acrylamide} (50:45:5 weight ratio)

A solution of 2-acrylamido-2-methylpropane-1-sulfonic acid, sodium salt (25.0 g, 0.109 mole), coupler monomer 4'-chloro-3'-[α-(4-methoxycarbonylphenoxy)-α-pivaloylacetamido]acrylanilide (22.5 g, 0.05 mole), N-(2-acetoacetoxyethyl)acrylamide (2.5 g, 0.013 mole), diisopropyl peroxycarbonate (0.5 g, 0.0024 mole) and 200 ml. of N,N-dimethyl formamide was purged with high purity nitrogen for 25 minutes and allowed to stand at 20° to 21° C. for about 12 hours. A clear viscous dope was obtained. The resulting polymer was isolated with isopropyl alcohol. The precipitate was washed with fresh alcohol, washed with diethyl ether, and dried at 20° to 25° C. under a rapid flow of nitrogen. The polymer was recovered as a light tan powder and had an inherent viscosity of 1.05 in N,N-dimethyl formamide.

A coating dope of this polymer was prepared and coated, dried, and crosslinked on gelatin-subbed poly(ethylene terephthalate) film base substantially as in Example 16. A clear, colorless, flexible, non-tacky layer of crosslinked polymer was formed on the film base. This layer was hard and impervious to water and rubbing.

EXAMPLE 18

Preparation and Use of a Magenta Dye Forming Polymeric Coupler,
Poly[2-acrylamido-2-methylpropane-1-sulfonic acid, sodium salt-co-1-(2,4,6-trichlorophenyl)-3-(3-acrylamidobenzamido)-2-pyrazoline-5-one-co-N-(2-acetoacetoxyethyl)acrylamide] (weight ratio 54:41:5)

This coupler polymer was prepared and tested in similar fashion to that in Example 17. The polymer had an inherent viscosity of 1.02 in N,N-dimethyl formamide. Upon crosslinking it formed a clear, colorless and hard layer which was impervious to water and rubbing.

EXAMPLE 19

Preparation and Evaluation of Photographic Element Comprising Yellow Dye Forming Polymeric Coupler The polymer of Example 17 was coated as a yellow dye forming coupler in a silver halide photographic element comprising a cellulose acetate film support having coated on one surface thereof a silver bromoiodide gelatin emulsion layer comprising (1) a silver bromoiodide emulsion (1.27 g Ag/m$^2$), gelatin (1.02 g/m$^2$) and the polymeric coupler 4.05 g/m$^2$), and (2) a protective overcoat layer comprising gelatin (1.07 g/m$^2$) and bis(vinylsulfonylmethyl) ether hardener (0.07 g/m$^2$).

The resulting photographic element was evaluated in the following manner to determine whether the polymeric coupler was effectively crosslinked so that it would not diffuse out of the element and into processing solutions.

Sample strips of the photographic element were soaked in a phosphate buffer bath (pH 12.0) at 38° C. for periods of from 0 to 20 minutes. After soaking, the strips were exposed on an Eastman 1B sensitometer and color developed (8 minutes, 38° C.), bleached, fixed, and washed in a high pH process of the type described in U.S. Pat. No. 3,046,129 (col. 23 and 24, color developer solution). The dye densities developed ($D_{max}$=2.50, 0 minute soak; $D_{max}$=2.46, 20 minute soak) at the various conditions showed very little effect from the high pH treatment. The similar dye densities obtained indicate that the polymeric coupler had become effectively crosslinked into the vehicle matrix and had not readily diffused into the high pH processing solution.

EXAMPLE 20

Preparation and Evaluation of Photographic Elements Comprising Cyan Dye Forming Polymeric Coupler The cyan polymeric coupler prepared in Example 15 was incorporated into a photographic element and tested as in Example 19. The polymer was found to be effectively crosslinked. It did not diffuse into the high pH processing solution.

EXAMPLE 21

Preparation and Evaluation of Photographic Elements Comprising Magenta Dye Forming Polymeric Coupler Several single layer silver bromoiodide photographic emulsions having couplers incorporated therein were coated on different samples of cellulose acetate film support. The resulting elements contained various levels of silver and the magenta dye forming polymer coupler described in Example 18 as shown in Table I below. Element A is the control and contains a conventional coupler solvent dispersion of the non-polymeric magneta-forming coupler 1-(2,4,6-trichlorophenyl)-3-{3-[α-(2,4-di-tert-amylphenoxy)acetamido]-benzamido}-5-pyrazolone. Elements B-E contained a polymeric coupler comprising the same magneta dye forming moiety.

Table I

| Element | Ag (g/m$^2$) | Magenta-Forming Coupler or Polymer (g/m$^2$) | Gelatin (g/m$^2$) |
|---|---|---|---|
| A (Control) | 1.52 | 0.74 | 1.39 |
| B | 1.52 | 1.21 | 0.82 |

Table I-continued

| Element | Ag (g/m²) | Magenta-Forming Coupler or Polymer (g/m²) | Gelatin (g/m²) |
|---|---|---|---|
| C | 3.02 | 1.53 | 1.10 |
| D | 4.74 | 1.53 | 1.65 |
| E | 3.02 | 2.56 | 1.10 |

Samples of these elements were then exposed on an Eastman 1B sensitometer and processed in either a conventional or modified reversal process of the type described in U.S. Pat. No. 3,046,129 (cols. 23 and 43). The color developer solution of the modified process contained a reduced level of sulfite (1.0 g/l) and no citrazinic acid. The resulting dye densities are recorded below in Table II.

Table II

| | Magenta $D_{max}$ | |
|---|---|---|
| Element | Normal Process | Modified Process |
| A (Control) | 1.80 | 2.96 |
| B | 0.37 | 1.36 |
| C | 0.50 | 1.70 |
| D | 0.63 | 2.14 |
| E | 0.66 | 2.38 |

From the $D_{max}$ data in Table II, it is clear that the polymeric coupler vehicle was effective at all levels of silver (g/m²) deposits used in the tests.

EXAMPLE 22

Cyan Dye Forming Coupler Composition Containing Polymer of Example 16 as Vehicle Two monochrome incorporated coupler silver halide photographic elements were prepared by coating one surface of each of two cellulose acetate film supports with a layer comprising a silver bromoiodide emulsion (coated to provide 1.08 g Ag/m²), a conventional coupler solvent dispersion of the non-polymeric cyan-forming coupler 1-hydroxy-2-{Δ-(2,4-ditertamylphenoxy)-n-butyl}naphthamide coated to provide 1.08 g coupler/m² and either (i) gelatin coated to provide 1.88 g/m² or (ii) a mixture of gelatin (38% by weight of mixture) and the polymer of Example 15 (62% by weight of mixture) coated to provide 1.17 g gelatin/m² and 0.71 g polymeric coupler/m², respectively. Each emulsion layer was then overcoated with a gelatin layer (0.98 g gelatin/m²) containing bis(vinylsulfonylmethyl) ether hardener (coated to provide 0.02 g/m², 1.5% total vehicle). All coating values are on a dry basis.

These cyan-forming combinations of dye forming coupler compositions and vehicles were exposed on an Eastman 1B sensitometer and processed in a reversal process of the type described in U.S. Pat. No. 3,046,129 (col. 23 and 24). The reslting sensitometer data and visual evaluations are recorded as follows:

| Dye Forming Coupler Composition | Vehicle | Dmax | Relative Speed | Physical Appearance |
|---|---|---|---|---|
| Element (i) | gelatin | 2.15 | 100 | Clear |
| Element (ii) | gelatin + polymer | 2.28 | 110 | Clear |

Similar testing of the yellow dye forming coupler composition containing the polymer of Example 17 provided similar results. These examples demonstrate the utility of the compounds of the present invention as vehicles and couplers for use in photographic elements.

It is seen from the data that the presence of the polymeric coupler improves Dmax and relative speed over conventional couplers without adversely affecting the physical appearance of the processed elements.

EXAMPLE 23

(Comparative example) Demonstration of Non-Crosslinkability of Dye Forming Polymeric Coupler Containing Units from 2-Acetoacetoxyethyl Methacrylate Monomer after Dialysis The polymeric color couplers of this invention can be effectively crosslinked with common photographic hardeners regardless of whether or not the polymers have been purified by conventional techniques. As previously indicated, this is not the case with similar compositions prepared with monomers disclosed in the prior art, such as those disclosed in U.S. Pat. No. 3,554,987, issued to Smith, e.g. 2-acetoacetoxyethyl methacrylate. The copolymers described in that reference have been generally found to have reduced capability of crosslinking after conventional purification techniques. The following test results illustrate this point.

To demonstrate the effect pof dialysis on a prior art polymer, poly{2-acrylamido-2-methylpropane-1-sulfonic acid, sodium salt-co-4'chloro-3'-[α-(4-methoxycarbonylphenoxy)-α-pivaloylacetamido]acrylanilide-co-2-acetoacetoxyethyl methacrylate} (weight ratio 50:45:5) was prepared by a procedure similar to that used for preparing the polymers of this invention. A series of coatings was then prepared in the manner as described in Example 16 from both dialyzed and undialyzed samples of the polymer using two crosslinking agents, formaldehyde and bis(vinylsulfonylmethyl) ether separately. Effective crosslinking was obtained in each case with the undialyzed polymer. However, the coatings prepared from dialyzed polymer dissolved and rapidly washed off in water, even without rubbing. Clearly, the dialyzed polymer samples failed to crosslink satisfactorily. In contrast, the coatings made with the polymer of Example 17 did not dissolve or rub off under the same conditions. The polymers of this invention, therefore, offer the advantage of providing crosslinkable polymers which are capable of crosslinking after purification as described herein.

Although this invention has been described in considerable detail with reference to certain preferred embodiments thereof, it will be understood that variations and modifications can be effected without departing from the spirit and scope of the invention.

We claim:

1. A radiation sensitive element comprising a support having thereon at least one radiation sensitive layer and a crosslinkable polymer of at least about 0.1 percent, by weight, of at least one polymerizable compound of formula (I):

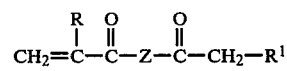

wherein R is hydrogen or methyl; $R^1$ is cyano or

wherein $R^2$ is alkyl; Z is —X—$R^3$—X— or

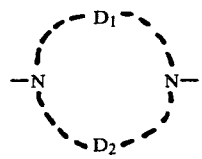

wherein each —X— is —O— or —$NR^4$—, provided at least one —X— is —$NR^4$—, wherein $R^4$ is hydrogen or alkyl, $R^3$ is divalent hydrocarbon and $D_1$ and $D_2$ together are the carbon atoms necessary to complete a 5 to 7 membered ring.

2. The element of claim 1 wherein said radiation sensitive layer comprises a photographic silver compound.

3. The element of claim 1 wherein Z is —$NH^4$—$R^3$—O—.

4. The element of claim 1 wherein Z is —NH—$R^3$—O— wherein $R^3$ is alkylene and $R^1$ is

5. The element of claim 1 wherein Z is

or —X—$R^3$—X—, wherein $R^3$ is alkylene, arylene, arylenealkylene, arylenebisalkylene or alkylenebisarylene.

6. The element of claim 1 wherein said polymerizable compound is N-(2-acetoacetoxyethyl)acrylamide, N-(2-acetoacetamidoethyl)methacrylamide, 4-acetoacetyl-1-methacryloylpiperazine, 4-acetoacetyl-1-acryloylpiperazine, acetoacetamidoethyl metacrylate or N-(3-acetoacetamidopropyl)methacrylamide.

7. The element of claim 1 wherein said polymer has an inherent viscosity in the range of from about 0.1 to about 3.0, as measured in N,N-dimethylformamide, acetone or 1 N sodium chloride.

8. The element of claim 1 wherein said polymer is of at least one polymerizable compound of formula (I) polymerized with up to 99.9 percent, by weight, of at least one additional polymerizable ethylenically unsaturated monomer.

9. The element of claim 8 wherein said additional polymerizable ethylenically unsaturated monomer is
(a) an acrylamide of formula (III):

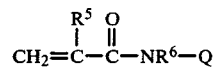

wherein each of $R^5$ and $R^6$ is hydrogen or alkyl and Q is a radical capable of undergoing oxidative coupling with a primary amino compound;
(b) a sulfoester or sulfonamide of formula (IV):

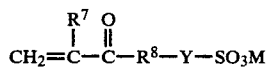

wherein $R^7$ is hydrogen or alkyl, $R^8$ is —O— or —$NR^9$—, wherein $R^9$ is hydrogen or alkyl, Y is a divalent aliphatic, alicyclic or aromatic radical, and M is a monovalent cation; or
(c) an amide of an ethylenically unsaturated carboxylic acid having a formula different from formula (III) or (IV).

10. The element of claim 9 wherein said additional polymerizable ethylenically unsaturated monomer is an acrylamide of formula (III).

11. The element of claim 9 wherein said polymerizable compound is N-(2-acetoacetoxyethyl)acrylamide, N-(2-acetoacetamidoethyl)methacrylamide, 4-acetoacetyl-1-methacryloylpiperazine, 4-acetoacetyl-1-acryloylpiperazine, acetoacetamidoethyl methacrylate or N-(3-acetoacetamidopropyl)methacrylamide and said additional polymerizable ethylenically unsaturated monomer is 2'-[2-(1-hydroxy-2-naphthoylamino)ethyl]acrylanilide, 4'-chloro-3'[α-(4-methoxycarbonylphenoxy)-α-pivaloylacetamido]acrylanilide, 1-(2,4,6-trichlorophenyl)-3-(3-acrylamidobenzamido)-2-pyrazoline-5-one, 2-acrylamido-2-methylpropane-1-sulfonic acid, 2-acrylamido-2-methylpropane-1-sulfonic acid, sodium salt or acrylamide.

12. The element of claim 1 wherein said polymer is in said radiation sensitive layer.

13. The element of claim 12 wherein said radiation sensitive layer comprises a hydrophilic colloid.

14. The element of claim 13 wherein said hydrophilic colloid is gelatin.

15. The element of claim 8 wherein said polymer is of from about 2 to about 30 percent, by weight, of at least one compound of formula (I) polymerized with from about 70 to about 98 percent, by weight, of said additional polymerizable ethylenically unsaturated monomer.

* * * * *

UNITED STATES PATENT AND TRADEMARK OFFICE
CERTIFICATE OF CORRECTION

PATENT NO. : 4,215,195
DATED : July 29, 1980
INVENTOR(S) : I. S. Ponticello, K. R. Hollister and R. C. Tuites It is certified that error appears in the above-identified patent and that said Letters Patent are hereby corrected as shown below:

Column 5, lines 64 and 65; change ">" to -- < --.

Column 8, line 15; change "cyanoactoxypropyl)methacrylamide/" to -- cyanoacetoxypropyl)methacrylamide/ --.

Column 8, line 27; change "acrylaniline" to -- acrylanilide --.

Column 11, line 52; change "TM" to --$^{TM}$ (superscript) --.

Column 14, line 40, change "2-acrylammido" to -- 2-acrylamido --.

Column 15, line 27; change "POly-" to -- Poly- --.

Column 17, line 54; change "reslting" to -- resulting --.

Column 18, line 25; change "pof" to -- of --.

Column 19, line 43; change "metacrylate" to -- methacrylate --.

Signed and Sealed this

Eleventh Day of November 1980

[SEAL]

Attest:

SIDNEY A. DIAMOND

Attesting Officer

Commissioner of Patents and Trademarks